US 6,561,352 B2

(12) United States Patent
Sherman et al.

(10) Patent No.: US 6,561,352 B2
(45) Date of Patent: May 13, 2003

(54) SHARPS DISPOSAL

(75) Inventors: Alan Sherman, 7639 Westmoreland Ave., St. Louis, MO (US) 63105; Wells Stone Bearinger, St. Louis, MO (US); Neil Erwin Koenig, St. Louis, MO (US)

(73) Assignee: Alan Sherman, St. Louis, MO (US)

( * ) Notice: Subject to any disclaimer, the term of this patent is extended or adjusted under 35 U.S.C. 154(b) by 0 days.

(21) Appl. No.: 09/772,705

(22) Filed: Jan. 30, 2001

(65) Prior Publication Data

US 2002/0100706 A1 Aug. 1, 2002

(51) Int. Cl.$^7$ ................................................ B65F 1/16
(52) U.S. Cl. .................................... 206/366; 206/370
(58) Field of Search ............................. 206/366, 370, 206/210; 588/255, 258; 422/22, 28; 219/68

(56) References Cited

U.S. PATENT DOCUMENTS

| | | | |
|---|---|---|---|
| 4,488,643 A | * 12/1984 | Pepper | 206/216 |
| 4,600,112 A | * 7/1986 | Shillington et al. | 206/366 |
| 4,779,728 A | 10/1988 | Hanifl et al. | |
| 4,816,307 A | * 3/1989 | Honeycutt | 206/366 |
| 4,828,107 A | * 5/1989 | Spencer | 206/366 |
| 4,900,500 A | 2/1990 | Honeycutt | |
| RE33,413 E | * 10/1990 | Hanifl | 206/366 |
| 5,080,251 A | * 1/1992 | Noack | 206/366 |
| 5,240,108 A | * 8/1993 | Tonna | 206/364 |
| 5,322,165 A | * 6/1994 | Melker et al. | 206/365 |
| 5,336,862 A | * 8/1994 | Yelvington | 219/68 |
| 5,401,444 A | * 3/1995 | Spinello | 264/0.5 |
| 5,415,315 A | * 5/1995 | Ramirez | 206/366 |
| 5,419,435 A | * 5/1995 | Perzan et al. | 206/366 |
| 5,538,132 A | 7/1996 | Propp et al. | |
| 5,630,506 A | * 5/1997 | Thorne et al. | 206/366 |
| 5,674,175 A | * 10/1997 | Bailey | 206/366 |
| 6,087,548 A | * 7/2000 | Levy et al. | 405/129.28 |
| 6,253,916 B1 | * 7/2001 | Bickel | 206/366 |

* cited by examiner

Primary Examiner—David T. Fidei
(74) Attorney, Agent, or Firm—Polster, Lieder, Woodruff & Lucchesi (57) ABSTRACT

A sharps disposal unit of the present invention includes a cover and a disposable container upon which the cover rests. The cover includes a drop slot in its top surface, a baffle sloping downwardly from an edge of the drop slot, and a heated well which holds a supply of a melted sealant which will solidify upon cooling. The disposable container has a top surface with a flap in it and preferably has accordioned walls. The flap is hinged along a hinge line and is pushed downwardly by plates in the cover to open the container. A peel-off label is removably, applied to the flap. The flap, when opened, form a second baffle below the cover baffle which slopes in an opposite direction of the cover baffle. A closure (such as a tie) is provided to hold the flap closed when the container is full, and it is time to dispose of the filled container. The sealant encases needle tips to reduce the possibility of sticks by used needles and can be drawn into the hollow shaft of used needles; the container flap reduces the possibility of sharps falling out of the container if the container is dropped; and, the double baffle system reduces the possibility of someone reaching inside of the unit and gaining access to the needles. The peel-off removable label reduces the amount of germs which contact the flap. Upon removal of the label, the container flap (and hence the outside of the container) will be substantially free of germs which would otherwise be deposited in the container by the sharps deposited in the container.

38 Claims, 10 Drawing Sheets

SHARPS DISPOSAL

CROSS REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to a sharps disposal unit, and, in particular, to a sharps disposal unit having a permanent top portion with a disposable bottom portion, which reduces the potential of one reaching inside of the sharps disposal unit, and which allows for coating of the sharp end and shaft of, for example, a used needle.

Current sharps disposal units are typically fully disposable—that is, when the unit is filled or partially filled with sharps (i.e., syringes, needles, scalpels, etc.) the unit is disposed of and replaced with a new unit. To help reduce contact with the sharps in the unit, the units typically advise that once the unit is filled to a predetermined fill line the unit should be disposed of and replaced with a new unit. The fill line usually corresponds to the unit being 70–80% full. However, many of the currently available units are opaque and do not provide any manner to determine how full the unit actually is. Thus, in practice, the unit is not disposed of until sharps are readily visible near the open top of the container, at which point the unit is filled past the fill line.

This method of use has inherent risks associated with it. If the container is accidentally dropped, it is likely that the sharps in the container will spill out of the container, requiring additional handling of potentially dangerous items. Additionally, sharps near the top of the container may be readily accessible to probing hands. These could be the hands of a patient, such as a curious child in a pediatrician's office. Further, the ease of accessibility to needles, even dirty needles, is a factor in medical facilities located in areas of high drug use, or where people break into doctors' offices to steal needles.

Several sharps disposal units have been designed which encase the complete syringe, for example. Although, these disposal units do make the needle inaccessible and unusable, there is no need to encase, for example, the syringe tube and plunger. To reduce the possibility of sticks, all that need be encased is the tip of the needle. Because these units encase the entire syringe, they use a significantly greater amount of encasing material than is necessary.

We know of no currently available unit which reduces the possibility of spillage or of accidental contact with the sharps contained within the unit. Nor do we know of any currently available unit which allows for easily sealing the sharp without encasing the complete sharp.

BRIEF SUMMARY OF THE INVENTION

Briefly stated, a sharps disposal unit of the present invention includes a cover and a disposable container. The cover has a front wall, a back wall, side walls, and a top surface. A drop slot is formed in the top surface through which sharps can be dropped A baffle slopes downwardly from an edge of the drop slot. A pair of arms or plates extend downwardly from the cover top surface. The plates have a length sufficient to engage the top of the container, as described below.

A heated, removable well or container is placed in the cover top surface to hold a supply of a liquid sealant, such as paraffin or hot melt glue, which will solidify upon cooling. The sealant can be colored and/or provided with a germicide. A removable lid is provided to cover the well. The lid is domed shaped, having a generally central opening and a funnel shaped surface surrounding the opening. The domed lid forms a space into which liquid sealant flows if the cover is tipped or dropped, thereby containing the substantially all sealant that would spill out of the well. The lid opening is sized to be slightly smaller than a finger, to prevent someone from inadvertently placing a finger in the heated well. Additionally, the lid, when placed over the well, creates a substantially enclosed chamber which traps the heat in the well. Prior to placing the needle into the unit, the medical personnel can dip the needle into the sealant. Preferably, the well of melted sealant is sufficiently deep to allow the complete shaft of the needle to be coated with the sealant. Gravity tends to cause a bulb of sealant or a thicker wall of sealant to form at the end of the needle to encase the needle and provide a dull tip at the end of the needle to reduce the possibility of sticks. A storage well can be positioned near the heated well to hold a supply of unmelted sealant.

The disposable container has side walls, a bottom, and a top. The side walls are preferably accordioned so that the container can be compressed during shipping and storage, and then expanded for use. A door or flap is formed in the container top. The container door is positioned beneath the cover drop slot and is opened by the cover plates when the container and cover are assembled together. When the container door is pushed or flexed inwardly by the cover plates, the door defines a second baffle, which slopes in an opposite direction of the cover baffle. The door is defined on three sides by slits in the container top surface. The container top surface is made of a flexible material having a "memory", such as a thermoplastic material. When the cover and container are separated, the container door will automatically move towards a closed position to be at least partially closed. To maintain the door in a fully closed position, the container top surface is provided with retainers. The retainers can be cable ties, twist ties or a barbed nylon cable with a lock device at one end to accept the notches or barbs of the cable and not allow them to loosen. The retainers are threaded through holes placed on opposite sides of the slit. The ends of the retainer extend up through the holes, and the tie traverses the slit along an underside of the container top surface. The retainers are used to secure the door in its closed position and traverse the slit along an upper side of the container top surface when pulled.

A bracket is provided to hold the cover and container together. The cover includes a shoulder along each of the side walls, and the shoulder includes a dip in an upper surface of the cover. Similarly, the container includes a bottom surface in an upper lip or neck of the container above the first accordion or pleat of the container. An upwardly curved dip is also formed in this surface. The bracket includes a pair of upper arms and a pair of lower arms. The upper and lower arms are spaced apart a distance approximately equal to the distance between the cover shoulder top surface and the container neck bottom surface, when the cover is on the container. The two arms of each pair are spaced apart horizontally a distance equal to the side-to-side width of the sharps disposal unit. The upper and lower arms each include a bend which engages the respective dips in the cover shoulder and the container neck surfaces to positively hold the cover and container together. The cover and container, which assembled together, can simply be slid into and out of the bracket. The bracket can be provided with a mounting plate to mount the unit on a wall or with a stand to stand the unit on a counter top.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

The following detailed description illustrates the invention by way of example and not by way of limitation. This description will clearly enable one skilled in the art to make and use the invention, and describes what we presently believe is the best mode of carrying out the invention.

A sharps disposal unit 1 of the present invention includes a cover 3 which is received on a disposable container 5. Unlike the prior sharps disposal units, the cover 3 is a permanent member, which is not disposed of. Rather, only the container 5 is disposed of. When the container 5 is full, it is closed, as described below, and disposed of in accordance with applicable regulations. The cover 3 is then assembled with a new container 5. Preferably, the container 5 is at least translucent, so that the level of sharps within the container 5 can be readily determined, so that the staff of a doctors office, hospital, clinic, etc. know when to dispose of the container 5. The walls of the container 5 can be translucent, or only a strip of one wall need be translucent. Because only the container 5 of the unit 1 is disposed of, as opposed to the complete unit as occurs with conventionally available units, the overall cost of using and manufacturing the unit 1 is reduced, as compared to conventionally available sharps disposal units.

Figure 2:
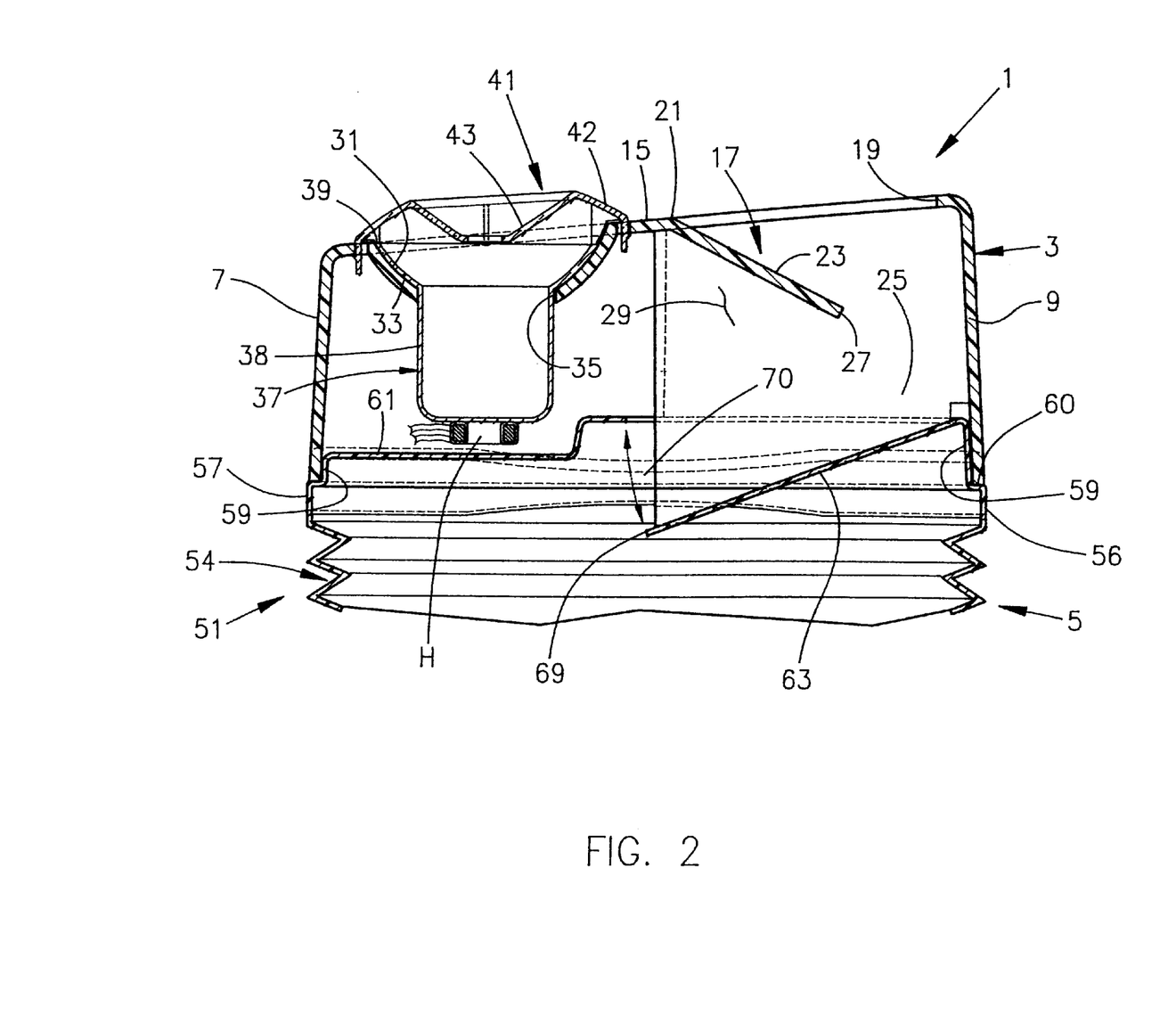
FIG. 2 is a cross-sectional view of the unit taken along line 2—2 of FIG. 1.
Figure 4:
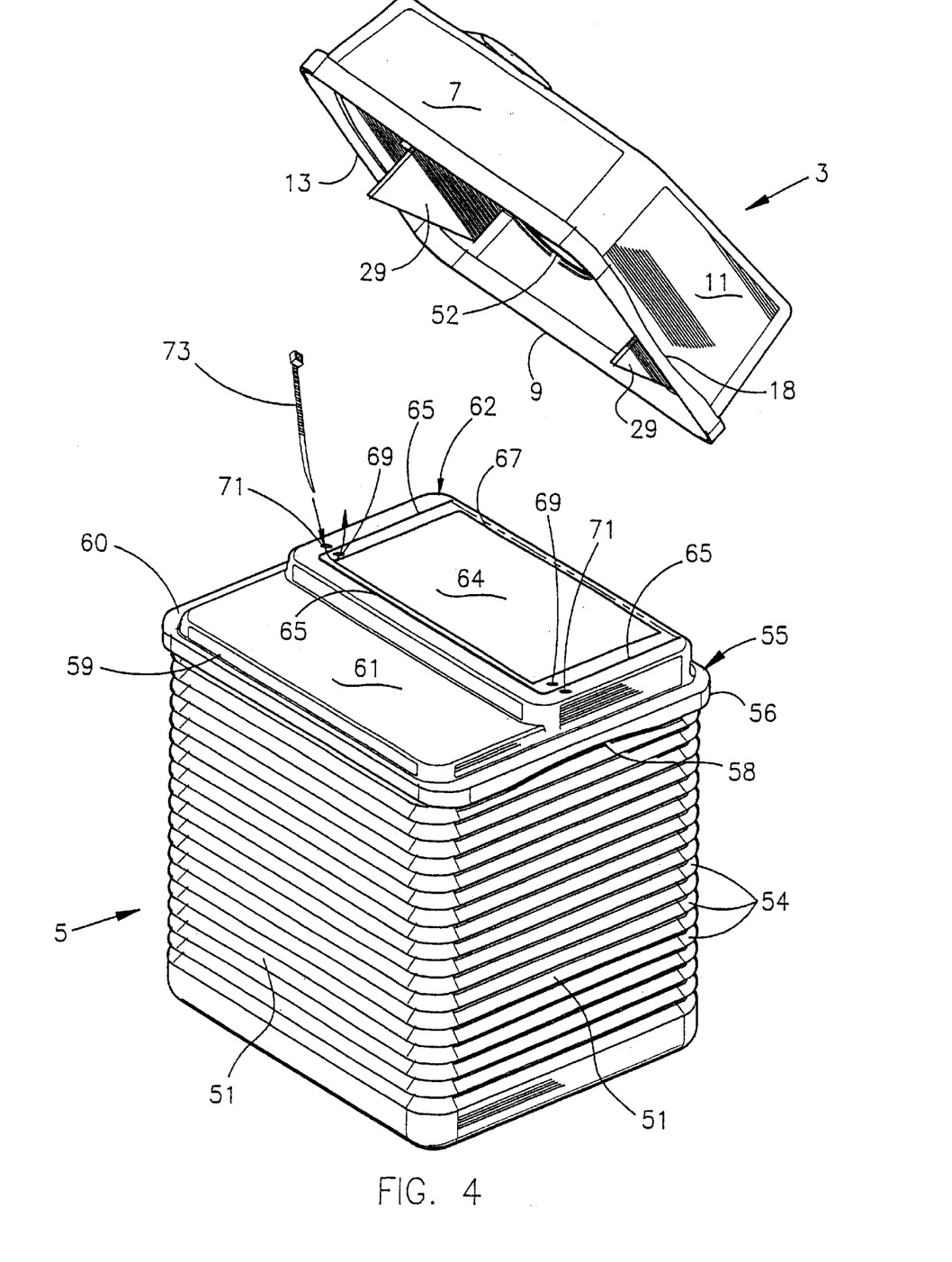
FIG. 4 is an exploded perspective view of the disposal unit.
Figure 5:
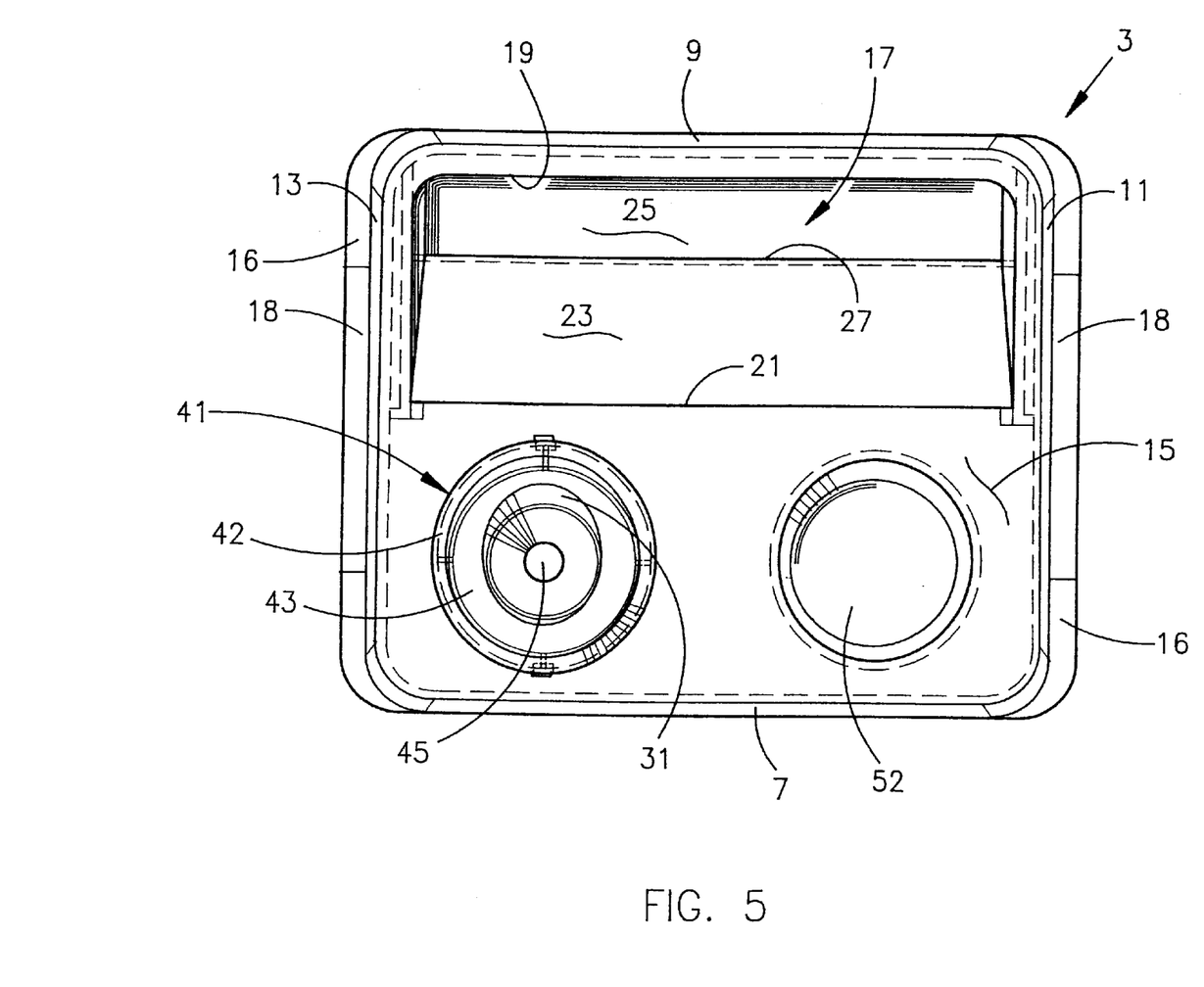
FIG. 5 is a top plan view of a cover of the disposal unit.

The cover 3 includes front, back, and side walls 7, 9, 11, and 13, and an upper surface 15. The cover 3 is opened on its bottom. A shoulder 16 having a dip 18 is formed on the side walls 11 and 13. A drop slot 17 is formed in the cover top surface 15. The back edge 19 of the drop slot 17 is spaced forwardly slightly from the back wall 9 of the cover 3; and the forward edge 21 of the drop slot is approximately midway between the cover front and back walls. Thus, at the surface 15, the drop slot has a front-to-back width equal to slightly less than about ½ the front-to-back depth of the cover 3. A baffle 23 (FIG. 2) extends diagonally downwardly and rearwardly from the drop slot front edge 21 to define a throat 25 through which sharps, such as syringes, drop. The back or edge 27 of the baffle is about ½ to ⅔ of the way back. Thus, the throat 25 through which a sharp drops has a width which is about ⅓ to ½ the width the drop slot 17 at the surface 15. The cover also includes a pair of plates 29 which extend downwardly from the bottom of the surface 15. The plates 29 are positioned on opposite sides of the top 3 and have a length sufficient to engage the container, as described below, to open the container. As best seen in FIGS. 2 and 4, the bottom edge of the plate 29 slopes downwardly, from the rear of the plate to the forward edge of the plate. As can be appreciated, the plates 29 form side walls for the drop slot 17 to prevent sharps from sliding off the sides of the baffle 23.

The drop slot 17 is in the back of the cover top surface 15. Forwardly of the drop slot 17, the cover 3 includes a contoured recess 31 having an arced side wall 33 with central opening 35. A container or well 37 having a cylindrical portion 38 and an annular rim 39 is received in the cover recess 31. The rim 39 is at the top of the cylindrical portion 38 and sits on the recess side wall 33 to support the container 37 in the cover 3. The curvature of the recess wall 33 and the curvature of the container rim 39 are substantially the same. The container 37 is heated, and contains a supply of liquid sealant S (i.e. paraffin, hot glue, etc.). The container 37 can be integral with the cover 3. However, the cover 3 is preferably injection molded of a thermoplastic material, and therefore, the container 37, which is preferably made from a metal or a different, heat resistant plastic, is a separate piece from the cover 3 and is slipped into the opening 35 in the cover recess 31. To heat the container, container 37 includes a heating element H, such as a resistance heating element. The heating element H is shown to be at the bottom of the container 37 in FIG. 6. However, it can also comprise resistance wires which surround the container cylinder 38. The heating element H can be energized with a battery or by means of an electrical cord which is plugged into a nearby electrical outlet in the room in which the unit 1 is placed. The heating element need be only hot enough to heat the sealant to its melting temperature and to maintain the sealant in a liquid state. The temperature of the container 37 will not affect the cover 3.

Figure 6:
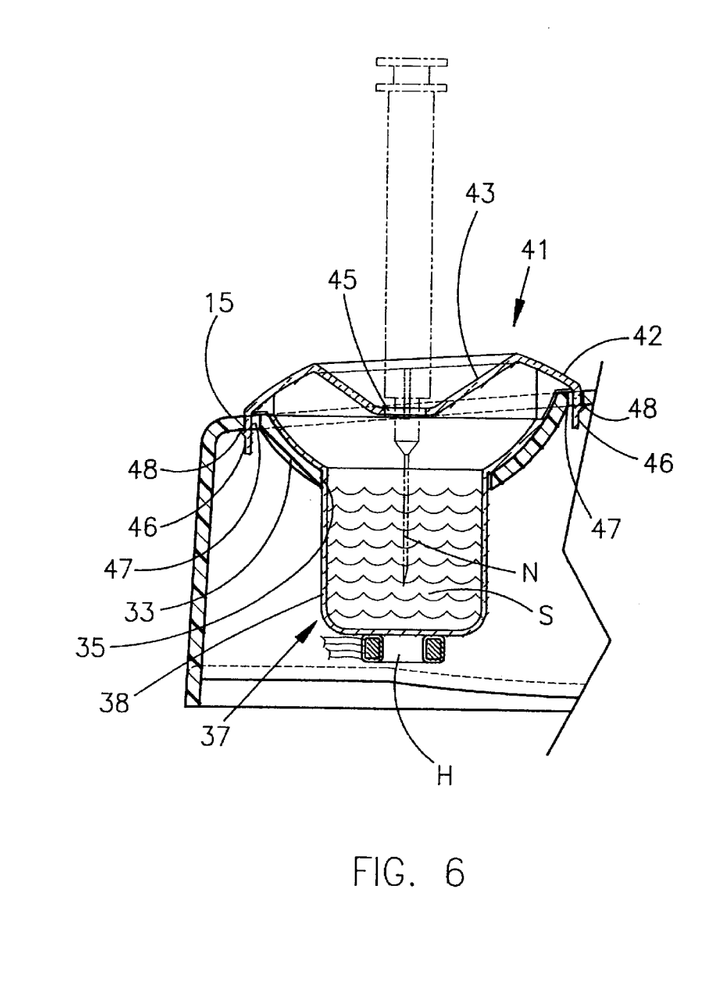
FIG. 6 is an enlarged cross-sectional view of a heated well of the cover, and a top for the well.
Figure 6A:
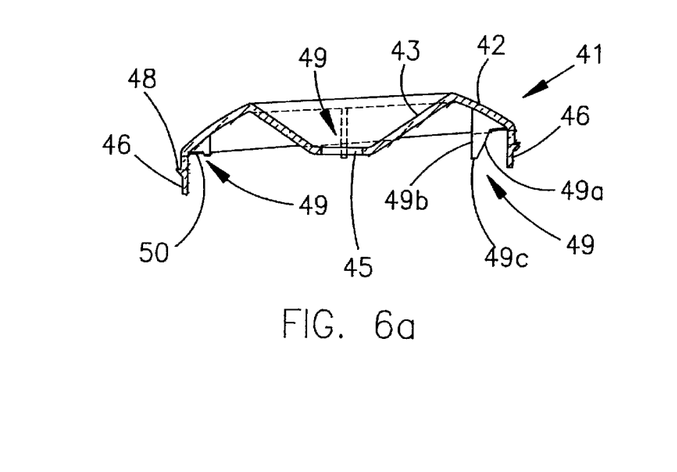
FIG. 6A is a cross-sectional view of the well lid.
Figure 7:
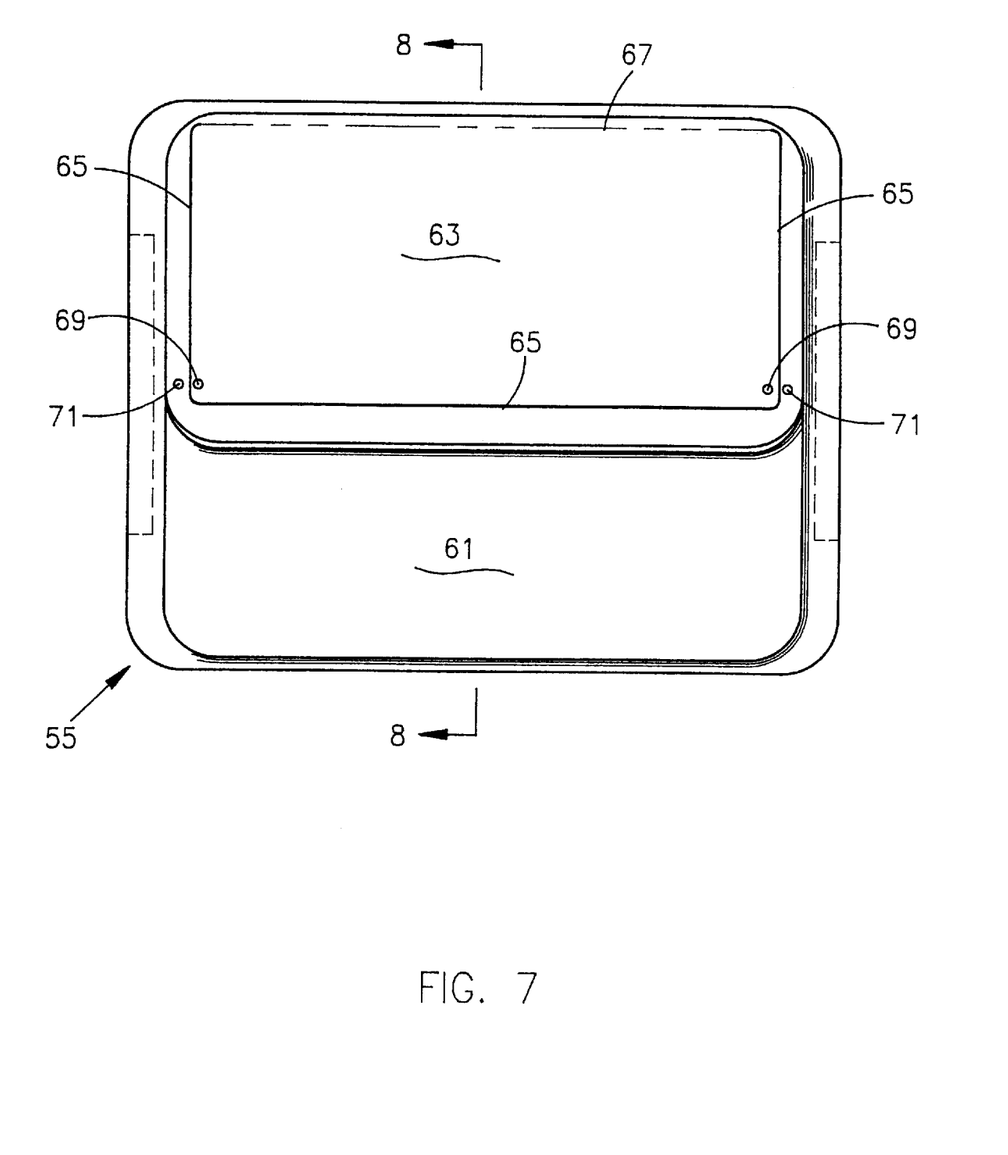
FIG. 7 is top plan view of a container of the disposal unit.
Figure 8:
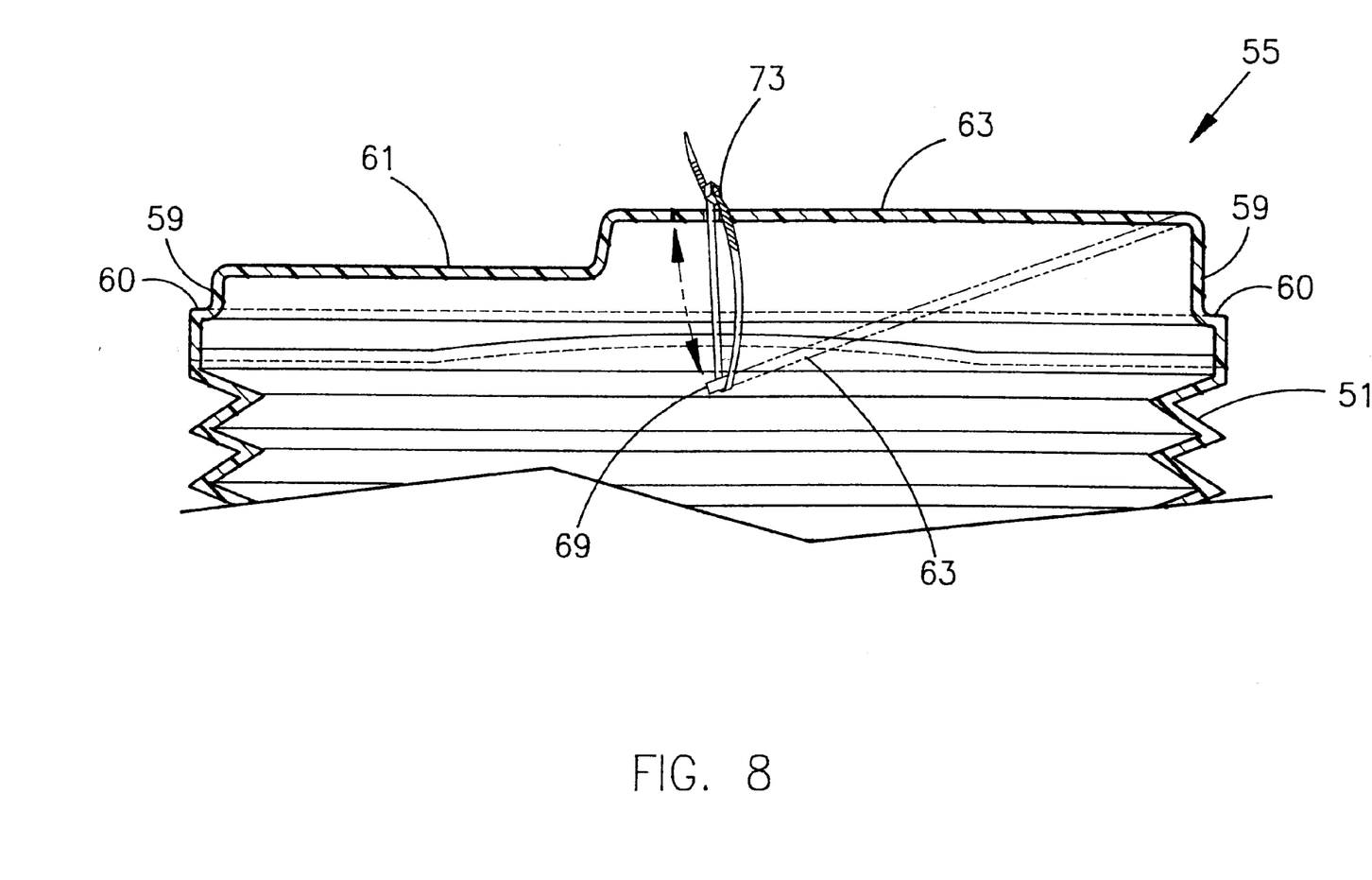
FIG. 8 is a fragmentary cross sectional view of the container taken along line 8—8 of FIG. 7, showing the container in its closed position and showing the container opened in phantom.

As seen in FIG. 6, the container is preferably sufficiently deep to accept the full length of the most commonly used needles N. The sealant can be used simply to coat the shaft of a used needle of a syringe by dipping the needle in the sealant. Once the syringe needle is removed from the sealant, the sealant will solidify on the needle, encasing the point and shaft of the needle. Usually, a bulb or area of thickened sealant will form at the end of the needle. This solidification and bulb formation will occur very shortly after the needle is removed from the reservoir. Because the needle is encased by sealant, any germs on the needle will be encased by the sealant. The bulb or thickened area of sealant at the end of the needle reduces the possibility of someone being stuck by a used needle. It also reduces the possibility of the needle piercing the container 5.

Additionally, the sealant can be drawn into the hollow core of the needle to prevent further use of the needle. If desired, the sealant can be colored (for example, the sealant can be red), to readily show that the needle has been previously used and cannot be used again. The sealant can also be formulated to include a germicide.

A domed lid 41 covers the container 37. The lid 41 has a domed outer surface 42 and a funnel shaped inner surface 43 having a central opening 45. The central opening 45 is sized to admit the needle N and the needle mount into the container 37. The opening 45 is also sized to be slightly smaller than a human finger to prevent someone from inadvertently sticking their finger in the heated well. The surface 43 is sized and shaped such that the distance between the lid opening 45 and the surface of the liquid sealant S allows for substantially all of the needle N to be coated with the sealant S. To mount the lid 41 to the cover 3, the lid 41 includes legs 46 which extend through openings 47 in the cover surface 15. The legs 46 include fingers 48 which snappingly engage the underside of the cover surface 15 to hold the well lid 41 to the cover surface 15. The lid 41 also includes four projecting legs 49 which depend from inner flanges 50. Each leg 49 has sloped outer surface 49a, a generally vertical inner surface 49b, and a generally flat bottom surface 49c. The flanges 50 rest on the cover top surface 15; and the leg bottom surface 49c sits on the upper edge of the well rim 33. As seen best in FIG. 6, the container 37 is situated to be generally vertical. However, the cover top surface 15 is somewhat sloped. Thus, the upper edge of the well rim 33 is close to the surface 15 at the front of the cover 3, and is farther below the surface 15 at the back of the cover surface 39. To allow for the top surface of the lid 41 to generally follow the same slope as the cover surface 15, one pair of legs 49 (i.e. the back pair of legs) is shorter than the opposite (i.e. front) pair of legs. Although the lid 41 is shown to include four legs 49, more or fewer legs could be used. Alternatively, the legs could be replaced with a sloped shoulder.

As seen in FIG. 6, the domed lid 41 defines a reservoir or space which will capture the liquid sealant if the unit 1 or cover 3 is inadvertently tipped or dropped. This will contain substantially all the sealant that would spill out of the well should the cover 3 be tipped or dropped. Additionally, the space defined by the lid above the well forms a zone which traps the heat of the well to help maintain the sealant in a liquid state.

Neither the lid 41 nor the container 37 are permanently fixed to the cover 3. Thus, the lid 41 can be removed from the container 37 and the container 37 can be removed from the cover 3. The removability of the lid 41 will allow for the container 37 to be cleaned. Further, the removability of the container 37 from the cover 3 will allow for replacement of the container 37 should the heating element cease functioning or should the container 37 need to be replaced for some reason. Thus, container 37 can be replaced or cleaned, without the need to remove the cover 3 from the container 5. Additionally, the removability of the container 37 allows for the container 37 to be positioned remote from or independently of the sharps disposal unit 1. This will allow for the container 37 to be closer to a patient or an outlet, when, for example, the disposal unit 1 is remote from the patient, or is remote from an outlet which will power the container 1.

The cover 3 additionally includes a storage well 52 near the heated container 37. The sealant which is used in the heated well can be supplied as small pieces of solid sealant. The storage well 41 is preferably sized to hold several pieces of the solid or unmelted sealant at once. As the level of liquid sealant in the container 37 lowers, pieces of sealant can simply be dropped in the container 37 and melted, to bring the level of the liquid sealant back to a desired level.

Figure 1:
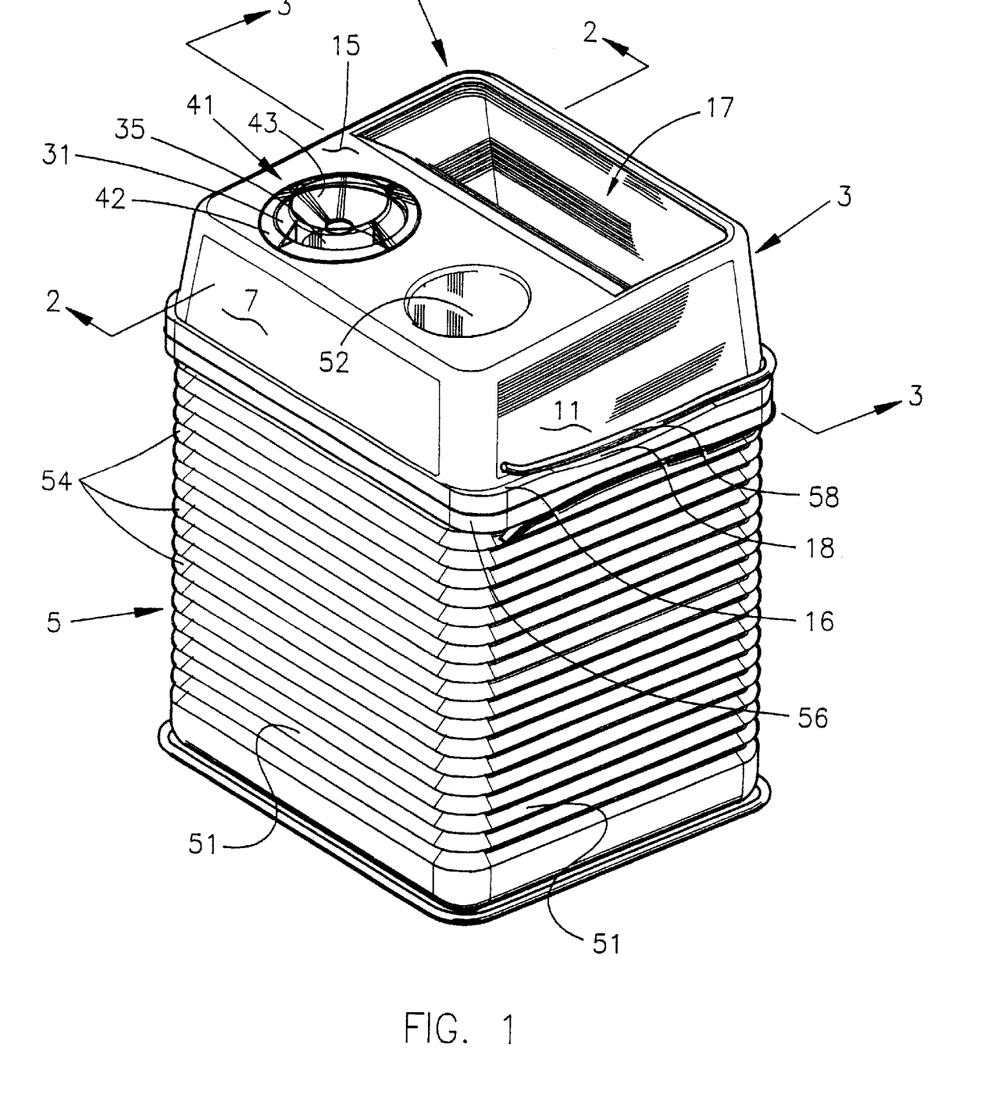
FIG. 1 is a perspective view of a disposal unit of the present invention.
Figure 3:
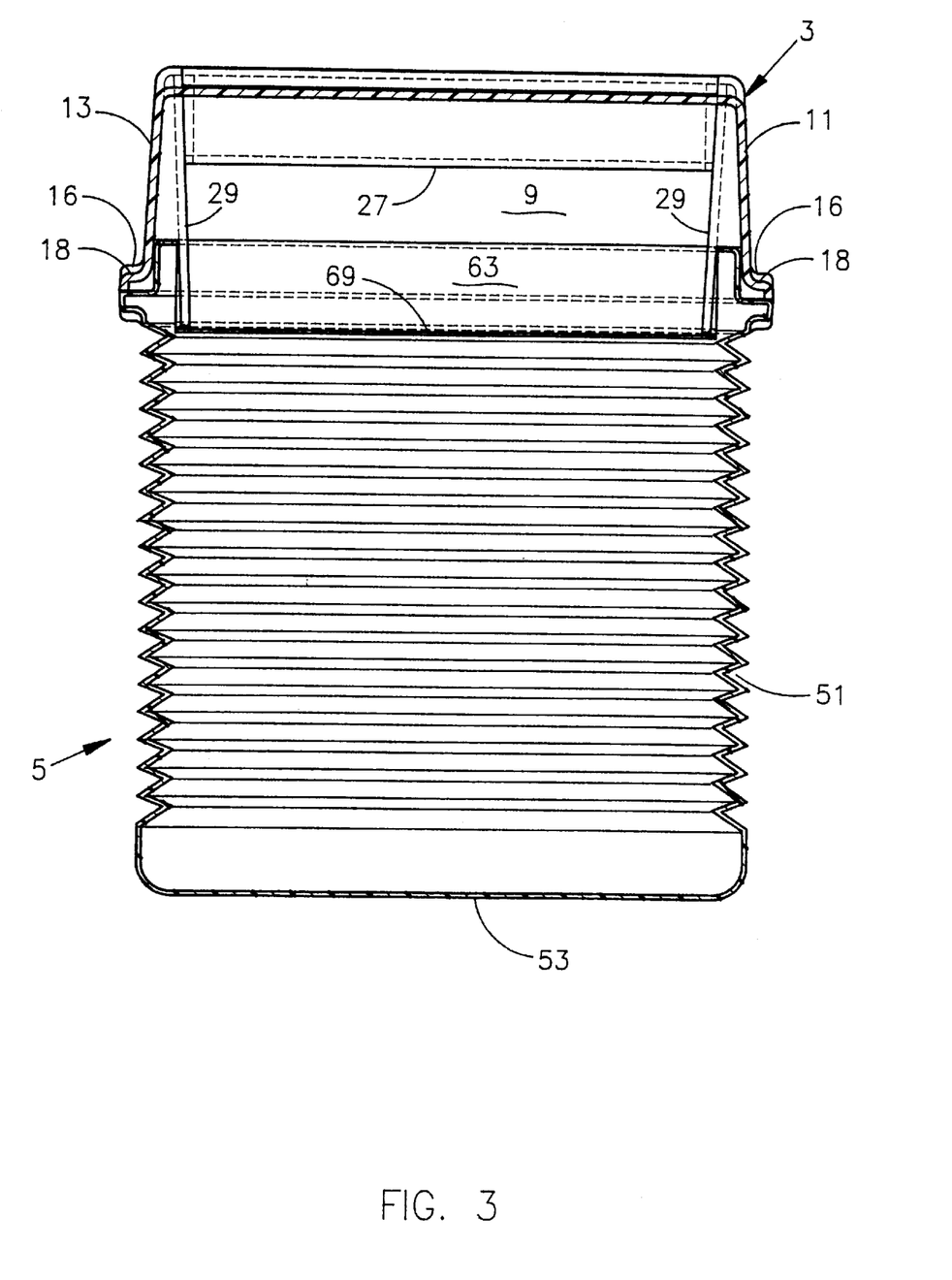
FIG. 3 is a cross-sectional view of the unit taken along line 3—3 of FIG. 1
Figure 10:
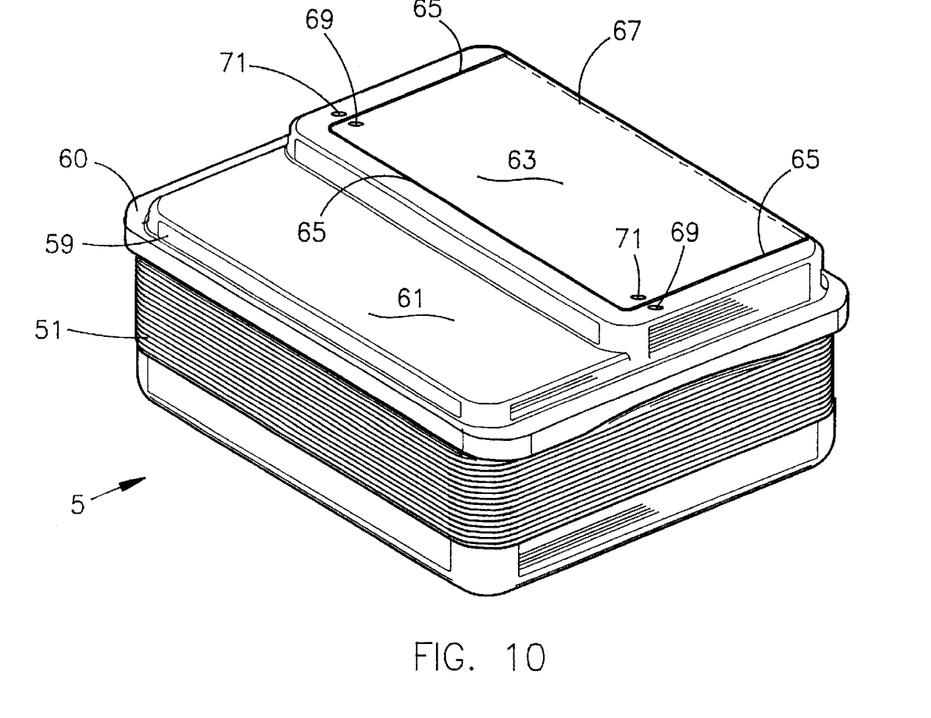
FIG. 10 is a perspective view of the container of the disposal unit in a compressed state.

The container 5 has four side walls 51, a bottom 53, and a top 55. The walls 51 are preferably accordioned, as seen in FIGS. 1–3, and have a plurality of pleats 54. The pleats 54 are positioned below a short top section or neck 56 having a concave indentation or dip 58 at its bottom surface. The accordioned walls allows the bottom portion 5 to be shipped and stored in a compressed state, as seen in FIG. 10. As can be appreciated, the containers 5 take up a fair amount of volume; and the ability to compress the containers 5 allows for a significantly greater number of containers 5 to be shipped and stored at once.

A short wall or lip 59 extends up from the inner edge of the neck 56. Thus, the lip 59 and neck 56 define a shoulder 60. As can be appreciated, the cover 3 sits on the container shoulder 60 and the lip 59 positions the cover 3 on the container 5. A top surface 61 extends across the wall 59 to close the container 5. As shown in the drawings, the top surface 61 is stepped to form a rear portion 62 which is above the forward portion of the top surface 61. The container is preferably blow molded, and hence, the top surface 61 is preferably integral with the lip 59. The container (including the walls, neck, and top) are preferably made from a blow-moldable thermoplastic, such as a polyethylene. The top surface could alternatively be a separate piece of thermoplastic material which is adhered (such as by gluing or welding) to the lip 59. A flap 63 is formed in a back portion 62 of the top surface 61. The flap 63 is defined on three sides by a slit 65 and flexes downwardly from the top surface. Preferably, there is no defined hinge line along which the flap flexes, to make better use of the "memory" of the flexible material from which the container top surface is made. The flap 63 extends toward the front of the container 5; thus, flap flexes about a line near the container wall 59 to allow the flap 63 to be deflected inwardly. A removable label 64 is applied to the top surface of the flap 63. The label 64 can be a pressure sensitive label which is adhered to the flap 63 using a weak adhesive, such as found on Post-It® notes, to allow the label to be easily removed. Alternatively, the label 63 can be formed from a plastic sheet, which adheres to the flap of its own accord. In either event, the label 64 preferably has a fluid impervious outer surface to provide a barrier against infectious germs that might otherwise contact the flap 63 when sharps are deposited in the container 5. As described below, the label 64 can be removed upon disposal of the container 5 so that the container top will be substantially free of germs. The label 64 can also be printed with instructions as to the proper use of the container.

Two pair of holes 69 and 71 are formed in the flap 63 and the top surface 61 towards the free end 69 of the flap 63. The holes 69 are formed in the flap 63 and the holes 71 are formed in the top surface 61. The holes 69 and 71 are formed on opposite sides of the slits 65 in pairs. A closure or retainer 73, such as a twist tie, a cable tie, or barbed nylon cables with a lock device at one end to accept the notches or barbs of the cable and not allow them to loosen is passed through each pair of holes, such that the closure 73 extends down through one hole 69 and up through the adjacent hole 71. The ends of the retainers thus extend up through the holes 69 and 71, and traverses the slot 65 along an underside of the surface 61. The opposite ends of the retainers are then connected. As can be appreciated, the retainers 73 limit the extent to which the flap 63 can drop into the container 5.

In use, the cover 3 is placed upon the container 5. As noted above, the bottom edge of the cover walls 7, 9, 11, and 13 rest on the container shoulder 60 and the cover is positioned on the container 5 by the lip 59. When the cover 3 is placed on the container 5, the cover plates 29 engage the flap 63 and deflect the flap 63 inwardly to open the container 5. As seen in FIG. 2, the container flap 63 is positioned below the cover baffle 23, and is sloped in the opposite direction of the cover baffle 23. Thus, the flap 63 defines a second baffle for the sharps disposal unit 1. The throat 25 of the cover 3 is above the back of the flap 63, and the space between free end 69 of the flap 63 and the container top surface 61 defines a second throat 70 for the sharps disposal unit. This second throat 70 is forward of the throat 25 and beneath the cover top surface 15. This configuration makes it extremely difficult to reach inside of the sharps disposal unit 1. Additionally, should the sharps disposal unit be dropped, the double baffle will substantially reduce the possibility of sharps falling out of the unit 1. Because the container top surface 61 is made from a material having a "memory", should the cover 3 separate from the container 5, the flap 63 will move to a relaxed and, at least partially, closed position, reducing the possibility of sharps spilling out of the unit 1.

When the container 5 is filled, it is simply separated from the cover 3. As noted above, the container is preferably at least partially translucent. That is, all the walls can be translucent, only one wall could be translucent, or one wall could include a vertical translucent strip. Thus, it is fairly easy to determine when the container 5 is filled. Because the container top surface 61 is made from a material with some memory, when the cover 3 is removed, the flap 63 will have a tendency return to at least a partially closed position. The closures 73 are pulled to raise the flap 63 until it is substantially flush with the container top surface 61 to completely close the container 5. The closures 73 are then operated (i.e., pulled) to secure the flap 63 in the raised, flush, and closed position. The filled container is then disposed of in the appropriate fashion, and a new container 5 is positioned beneath the cover 3.

Prior to closing of the container 5, the label 64 is removed from the container flap 63 and dropped into the container 5. Because the label 64 has a fluid impervious layer, any contaminants, such as blood, which might contact the label, do not contact the flap 63. Thus, the flap 63 is substantially free of any infections material or contaminants, and hence, the outer surface of the container 5 can be handled without a substantial fear of infection.

Figure 9:
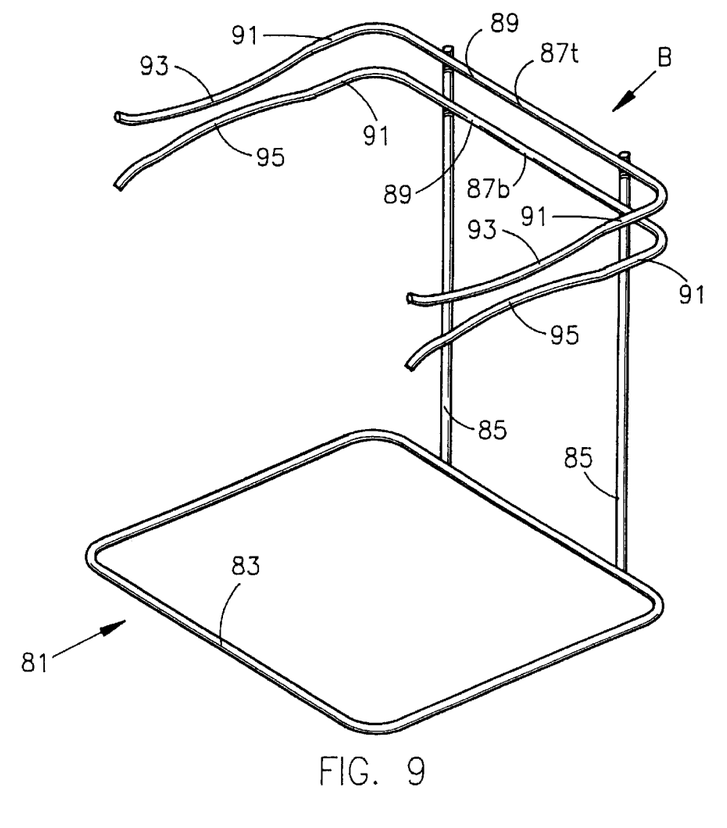
FIG. 9 is a perspective view of a bracket for the disposal unit incorporating a stand to position the disposal unit on a counter top.

As can be appreciated, the container 5, due to its accordioned walls 51, has a somewhat reduced amount of columnar strength. The weight of the cover 3 may thus cause the container 5 to compress. To prevent this, a bracket B is provided. In FIG. 9, the bracket is configured as a stand 81 to allow the disposal unit to be placed on a counter top. The stand 81 has a bottom 83, a pair of back arms 85 extending up from the bottom, and a pair of vertically spaced apart generally C-shaped members 87t and 87b. The members 87t and 87b in combination define the bracket B. Each member has a back section 89 which extends between the back arms 85 and opposed forwardly extending arms 91. The arms 91 of the upper member 87t have a downward curve 93 formed along their length; and the arms 91 of the lower member 87b have an upward curve 95 formed along their length. The C-members 87t and 87b are spaced apart vertically a distance approximately equal to the distance between the cover shoulder 16 and the bottom surface of the container neck 56. The curved ends 93 and 95 of the members 87t and 87b, respectively, engage the dip 18 in the cover shoulder 16 and the indentation 58 in the container neck 56. The engagement of the members 87t and 87b on the container and cover is a snap engagement, and the members 87t and 87b coact with the cover 3 and container 5 to hold the cover 3 on the container 5. As can be appreciated, after the cover and container are put together, the two are simply slid into the bracket to hold the cover 3 and container 5 together. To dispose of the container, the container and cover are simply pulled out of the bracket. The interaction of the curved ends of the bracket arms with the indentations or dips in the container and cover surfaces prevent the disposal unit 1 from accidentally sliding out of the bracket.

Figure 9A:
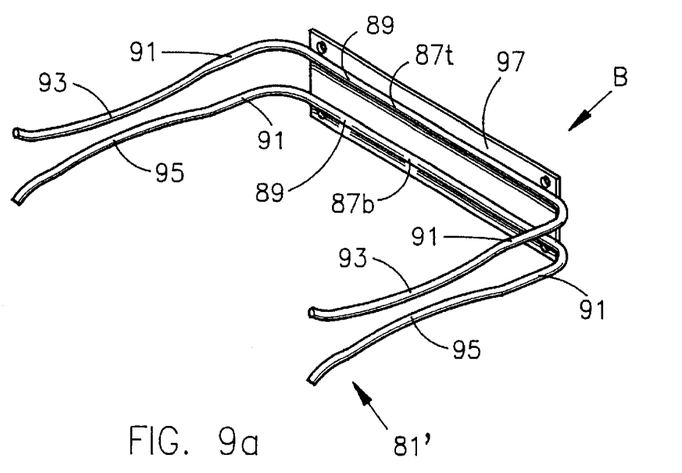
FIG. 9A is a perspective view of the bracket including a mounting plate for mounting the disposal unit on a wall.

The bracket can alternatively be provided with a mounting plate 97, as seen in FIG. 9a. The plate 97 includes screw holes to allow the bracket B to be mounted to a wall.

As can be seen, the sharps disposal unit 1 has many advantages. The use of the sealant which covers the needle and forms a bulb at the end of the sharps not only encases whatever germs may be on the needle, but reduces the possibility of a needle, for example, piercing the wall of the container. The bulb also presents a dull end, reducing the possibility of a stick by a used needle. If desired, sealant can be drawn into the hollow needle shaft to further reduce the possibility of a second use of the needle. The closeable container allows for easy dispensing of the container once it is filled, and the provision of the ties 73 allow for the flap or door 63 to be locked without any need to reach into the container. Thus, the personnel should not come into contact with the sharps in the container 5 when closing the container 5. Additionally, as noted above, the flap 63 substantially reduces the possibility of syringes coming out of the container should the container be dropped. Further, the corrugated or accordioned wall of the container allows the container to be compressed during shipping and storage. Depending on the number of corrugations or accordion pleats, the container can be reduced in size by as much as 40%. This substantially reduces the storage space required by the containers as well as the shipping cost of the containers. The double baffle formed by the cover and container, and the automatic closing of the container upon separation from the cover, make the disposal unit easy to use and reduces to possibility of sharps spilling out of the container. The container's translucency allows for the container to be filled to a greater capacity than conventional containers.

Figure 11:
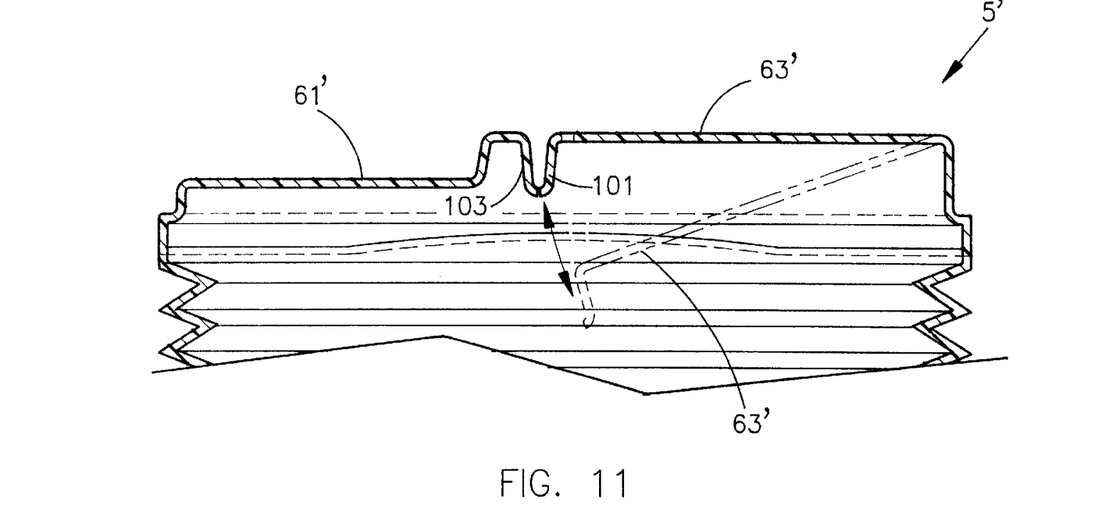
FIG. 11 is a cross-sectional view of a second embodiment of container for the disposal unit.

A second embodiment of the disposable container is shown in FIG. 11. The container 5' is substantially similar to the container 5 of FIG. 4. However, the flap 63' in the top surface 61' is provided with a lip or return 101 at its forward, free end. A similar lip or return 103 is provided in the top surface 61' adjacent, and substantially parallel to, the lip 101. The lips 101 and 103 provide extra rigidity to the flap 63' and the top surface 61', respectively. When the flap 63' is opened, as shown in phantom in FIG. 11, the lips 101 and 103 form baffles in the container which prevent syringes from piling up near the opening of the container. This further reduces the possibility of syringes (or other sharps) from inadvertently (coming out of the container, for example, if the container were dropped. Although the container 5' is shown with both lips 101 and 103, one of the lips could be eliminated so that the container 5' would only have one of the lips 101 and 103.

As various changes could be made in the above constructions without departing from the scope of the invention, it is intended that all matter contained in the above description or shown in the accompanying drawings shall be interpreted as illustrative and not in a limiting sense. For example, the lip 59 of the container 5 can be provided with small projections along its sides to create a tight fit between the cover 3 and the container 5, to reduce the possibility of the cover 3 inadvertently separating from the container 5. The baffles 23 and 63 could be reversed, such that the baffle 23 extends forwardly (rather than rearwardly) and the baffle 63 could extend rearwardly (rather than forwardly). The plates 29 could be replaced with downwardly extending arms or posts which push open the flap 63 of the container 5. Although not as desirable, the plates 29 of the cover 3 could be omitted, and the hinge line 65 for the container flap 63 could be formed such that the flap 63 will open under gravity when, for example, a syringe is dropped in the unit 1. The walls of the container 5 can be straight, rather then accordioned, if desired. The curved portions of the bracket arms could be moved, for example to the forward end of the arms. All that is required is that the curved portions of the bracket arms align with the dips or indentations in the cover shoulder 16 and the container neck 56. These examples are merely illustrative.

Having thus described the invention, what is claimed and desired to be secured by Letters Patent is:

1. A sharps disposal unit including:
    a cover having front, back, side walls, a top surface, and a drop slot in the top surface through which sharps can be dropped;
    a disposable container positioned beneath the cover; the disposable container having side walls, a bottom, a top, and a door formed in the top; the door being positioned beneath the cover drop slot and being opened when the container and cover are assembled together; and
    a member which depends from an inner surface of said cover top surface; said member engaging said container door to open said container door and maintain said container door open while said cover is on said container.

2. The sharps disposal unit of claim 1 wherein said container door comprises a flap formed in said container top; said container top being made of a material having a memory; whereby, when said container is separated from said cover, said door automatically moves to at least a partially closed position.

3. The sharps disposal unit of claim 2 wherein the disposable container includes a downwardly extending lip at a free end of said flap and/or a downwardly extending lip on said container top surface and adjacent the free end of said flap.

4. The sharps disposal unit of claim 1 wherein said cover includes a baffle which slopes downwardly from an edge of said drop slot; said container door forming a flap which opens into said container; said flap defining a sloped surface; said flap sloping in a direction opposite of the direction of said cover baffle.

5. The sharps disposal unit of claim 1 wherein said container walls are accordioned, said container being movable between a compressed state for shipping and storage and an expanded state for receiving sharps.

6. A sharps disposal unit including:
    a cover having front, back, side walls, a top surface, and a drop slot in the top surface through which sharps can be dropped; said cover including a heated container; said container being filled with a liquid sealant which solidifies upon cooling; and
    a disposable container positioned beneath the cover; the disposable container having side walls, a bottom, a top, and a door formed in the top; the door being positioned beneath the cover drop slot and being opened when the container and cover are assembled together.

7. The sharps disposal unit of claim 6 wherein said heated container is separate from said cover; said cover including an opening through which said container is inserted; said container including a rim which rests on a surface of said cover.

8. The sharps disposal unit of claim 6 wherein said heated container is removable from said cover.

9. The sharps disposal unit of claim 6 wherein said sealant is colored.

10. The sharps disposal unit of claim 6, wherein said sealant contains a germicidal agent.

11. The sharps disposal unit of claim 6 including a lid for said heated container, said lid including an opening through which a needle can be passed to coat the needle with said liquid sealant and/or to draw said liquid sealant into the needle, said liquid sealant solidifying upon cooling making the needle unusable for a subsequent injection.

12. The sharps disposal unit of claim 11 wherein said lid has a sloped wall surrounding said opening.

13. The sharps disposal unit of claim 11 wherein said lid is domed.

14. The sharps disposal unit of claim 11 wherein said lid is removably mounted to said cover top surface.

15. The sharps disposal unit of claim 6 including a storage well sized to hold sealant in a solid form.

16. A sharps disposal unit including:
    a cover having front, back, side walls, a top surface, and a drop slot in the top surface through which sharps can be dropped; and
    a disposable container positioned beneath the cover; the disposable container having side walls, a bottom, a top, and a door formed in the top; the door being positioned beneath the cover drop slot and being opened when the container and cover are assembled together; said container door comprising a flap which flexes inwardly; said flap being defined by a slit in said container top surface; said container including a retainer to hold said flap closed; said container including at least one opening in said flap and at least one opening in said container top surface; said openings being on opposite sides of said slit and adjacent each other; said retainer comprising a member having ends which extend up through said holes, said ends of said retainer member cooperating with each other to hold said container flap closed; said member traversing said slit along a bottom of said container top surface.

17. A sharps disposal unit including:
    a cover having front, back, side walls, a top surface, a drop slot in the top surface through which sharps can be dropped, a baffle which slopes downwardly from an edge of said drop slot, and a member which depends from an inner surface of said cover top surface; and
    a disposable container positioned beneath the cover; the disposable container having side walls, a bottom, a top, and a door formed in the top; the door being positioned beneath the cover drop slot and being movable between an upper closed position and a lowered open position; said cover member engaging said container door when said cover is placed on said container to open said door; said container door defining a container baffle beneath said cover baffle which slopes downwardly into said container; said container baffle being beneath said cover baffle and sloping in an opposite direction of said cover baffle.

18. The sharps disposal unit of claim 17 wherein said door is defined by a slit in said container top surface; said container including at least one opening in said flap and at least one opening in said container top surface; said openings being on opposite sides of said slit and adjacent each other; said sharps disposal unit further including a retainer member to hold said flap in a closed position; said retainer member comprising an elongate member having ends which extend up through said holes, said retainer member ends cooperating with each other to hold said lid closed; said member traversing said slit along a bottom of said container top surface.

19. A sharps disposal unit including a cover having a drop slot through which sharps can be dropped, a sharps container into which sharps fall, and a sealant container defining a chamber; said sealant container being separate from said sharps container, said sealant container chamber being heated; said sealant container chamber being at least partially filled with a liquid sealant which solidifies upon cooling.

20. The sharps disposal unit of claim 19 wherein said sealant container is separate from said cover; said cover including an opening through which said sealant container is inserted; said sealant container including a rim which rests on a surface of said cover.

21. The sharps disposal unit of claim 20 wherein said sealant container is removable from said cover.

22. A sharps disposal unit including a cover having a drop slot through which sharps can be dropped, a container into which sharps fall, and a sealant container defining a chamber; said chamber being heated; said chamber being at least partially filled with a liquid sealant which solidifies upon cooling; the sealant chamber including a lid, said lid including an opening through which a needle can be passed to coat the needle with said liquid sealant and/or to draw said liquid sealant into said needle, said liquid sealant solidifying upon cooling making the needle unusable for a subsequent injection.

23. The sharps disposal unit of claim 22 wherein said lid has a funnel shaped wall surrounding said opening.

24. The sharps disposal unit of claim 22 wherein said lid is domed.

25. The sharps disposal unit of claim 22 wherein said lid is removably mounted to said cover top surface.

26. The sharps disposal unit of claim 19 wherein said sealant is a paraffin or a hot melt glue.

27. The sharps disposal unit of claim 19 wherein said sealant is colored.

28. The sharps disposal unit of claim 19 wherein said sealant includes a germicide.

29. The sharps disposal unit of claim 19 wherein said disposal unit includes an electrical heating element which heats said chamber.

30. A sharps disposal unit including:
   a cover having front, back, side walls, a top surface, a drop slot in the top surface through which sharps can be dropped, a baffle which slopes downwardly from an edge of said drop slot, and a well defining a chamber; said chamber being heated; said chamber being at least partially filled with a liquid sealant which solidifies upon cooling; and
   a disposable container positioned beneath the cover; the disposable container having side walls, a bottom, a top, and a door formed in the top; the door being positioned beneath the cover drop slot and being movable along a hinge line between an upper closed position and a lowered open position; said side walls being accordioned; said disposable container being movable between a compressed state and an expanded state.

31. The sharps disposal unit of claim 30 including a member which depends from an inner surface of said cover top surface; said member pushing said container door to said open position.

32. The sharps disposal unit of claim 30 including a bracket; said bracket including a pair of upper arms and a pair of lower arms; said cover including a surface over which said bracket upper arms slide; said container including a surface under which said bracket lower arms slide; said upper and lower arms being spaced apart a distance approximately equal to the distance between said cover surface and said container surface; said bracket holding said cover and container together.

33. The sharps disposal unit of claim 32 wherein said cover surface includes a downwardly curved depression and said container surface includes an upwardly curved depression; said bracket upper arms having a downwardly curved end and lower arms having an upwardly curved end; said curved ends of said bracket arm engaging said depressions of said cover surface and container surface to snappingly receive said container and cover.

34. The sharps disposal unit of claim 32 said bracket includes a wall mount to enable said unit to be mounted on a wall.

35. The sharps disposal unit of claim 32 wherein said bracket includes a stand to enable said unit to be placed on a counter.

36. The sharps disposal unit of claim 30 includes a removable label on said container door.

37. A sharps disposal unit including:
   a cover having front, back, side walls, a top surface, a drop slot in the top surface through which sharps can be dropped, a baffle which slopes downwardly from an edge of said drop slot;
   a disposable container positioned beneath the cover which receives sharps dropped through said drop slot of said cover; said disposable container being removable from said cover; and
   a bracket including a pair of upper arms and a pair of lower arms; said cover including a surface over which said bracket upper arms slide; said container including a surface under which said bracket lower arms slide; said upper and lower arms being spaced apart a distance approximately equal to the distance between said cover surface and said container surface; said bracket holding said cover and container together.

38. The sharps disposal unit of claim 37 wherein said cover surface includes a downwardly curved depression and said container surface includes an upwardly curved depression; said bracket upper arms having a downwardly curved end and lower arms having an upwardly curved end; said curved ends of said bracket arm engaging said depressions of said cover surface and container surface to snappingly receive said container and cover.

* * * * *